United States Patent [19]
Kikuchi et al.

[11] Patent Number: 5,626,751
[45] Date of Patent: May 6, 1997

[54] FILTER UNIT AND HIGH-PRESSURE SIZING APPARATUS

[75] Inventors: Hiroshi Kikuchi; Hitoshi Yamauchi, both of Tokyo; Kiyoto Yachi, Chiba; Hiroshi Honda, Matsudo; Norio Suzuki, Chiba; Akinori Hoshio; Takazo Hirose, both of Kanagawa-ken, all of Japan

[73] Assignees: Daiichi Pharmaceutical Co., Ltd., Tokyo; Nomura Micro Science Co., Ltd., Kanagawa-ken; NOF Corporation, Tokyo, all of Japan

[21] Appl. No.: 91,714

[22] Filed: Jul. 15, 1993

[30] Foreign Application Priority Data

| Jul. 15, 1992 | [JP] | Japan | 4-187905 |
| Jul. 15, 1992 | [JP] | Japan | 4-187911 |
| Aug. 25, 1992 | [JP] | Japan | 4-225645 |

[51] Int. Cl.$^6$ .................... B01D 63/00; B01D 29/05; B01D 35/30
[52] U.S. Cl. ............ 210/321.75; 156/253; 156/308.4; 210/149; 210/321.84; 210/484; 210/498; 252/314; 264/4.3; 424/450
[58] Field of Search .............. 210/321.6, 321.64, 210/321.75, 321.84, 446, 451, 484, 173, 455, 483, 149, 498; 241/70, 77, 72, 95

[56] References Cited

U.S. PATENT DOCUMENTS

| 2,073,991 | 3/1937 | Koser . | |
| 2,256,717 | 9/1941 | Kors . | |
| 3,361,261 | 1/1968 | Fairey et al. | 210/314 |
| 3,836,464 | 9/1974 | Brookins et al. | 210/413 |
| 4,493,815 | 1/1985 | Fernwood et al. | 210/455 X |
| 4,737,323 | 4/1988 | Martin et al. | 210/500.26 X |
| 4,869,821 | 9/1989 | Korin | 210/321.64 |
| 4,871,456 | 10/1989 | Narao et al. | 210/321.84 |
| 4,927,637 | 5/1990 | Morano et al. | 424/450 |
| 5,008,050 | 4/1991 | Cullis et al. | 264/4.3 |
| 5,215,657 | 6/1993 | Goldfield et al. | 210/321.64 |

OTHER PUBLICATIONS

E. Mayhew et al., "An Advanced Technique for the Manufacture of Liposomes", *American Biotechnology Laboratory*, vol. 3, No. 6, Nov./Dec. 1985, pp. 36–41.

L.D. Mayer et al., "Vesicles of Variable Sizes Produced by a Rapid Extrusion Procedure", *Biochimica et Biophysica Acta*, 858 (1986) pp. 36–41.

M.J. Hope, "Production of Large Unilamellar Vesicles by a Rapid Extrusion Procedure. Characterization of Size Distribution, Trapped Volume, and Ability to Maintain a Membrane Potential", *Biochimica et Biophysica Acta*, 812 (1985) pp. 55–65.

*Primary Examiner*—Richard D. Lovering
*Attorney, Agent, or Firm*—Henderson & Sturm

[57] ABSTRACT

A filter unit comprises a metallic supporting plate possessed of stepped through holes opening with a larger diameter in one main surface and with a smaller diameter in the other main surface (wherein the diameter ratio of larger-diameter openings to smaller-diameter openings is desired to be in the range of 1:0.01 to 1:0.5) or a pressureproof supporting plate having in one surface thereof inclined liquid flow grooves arranged in a radial pattern and concentric circular liquid flow grooves adapted to intersect the radially arranged liquid flow grooves and a membrane filter disposed on the surface of the supporting plate containing larger-diameter openings or liquid flow grooves. This filter unit is ideally used for finely dividing and uniformly sizing suspended lipid particles assuming a definite average particle size and a specific particle size distribution. The high-pressure sizing apparatus and the method for production of suspended lipid particles utilize the filter unit constructed as described above and rely essentially for their operation on effecting fine division of lipid particles in the suspension by supplying the suspension of lipid particles from the membrane filter side under pressure and causing the suspension to pass through the membrane filter. Thus, they constitute themselves effective measures for pharmacological products and cosmetic products which are in need of lipid particles assuming a definite average particle size and a specific particle size distribution.

14 Claims, 7 Drawing Sheets

FILTER UNIT AND HIGH-PRESSURE SIZING APPARATUS

BACKGROUND OF THE INVENTION

1. Field of the Invention

This invention relates to a filter unit suitable for the production of suspended lipid particles represented by emulsions and liposomes, a high-pressure sizing apparatus, a method for the production of suspended lipid particles finely divided uniformly (homogeneously) within a prescribed range, and a method for the production of a membrane filter cassette.

2. Description of the Related Art

Suspensions of lipid, particles such as, for example, emulsions having water and oil emulsified by the use of amphophilic lipids and liposomes possessed of an internal water core, and allowed to form a closed lipid bilayer membrane are known to those skilled in the art. The suspension of lipid particles of this type or class have been arousing much interest in the feasibilization thereof in applications for example to such pharmacological products as antitumor drugs and anti AIDS drugs, applications to products of the food industry, and applications to products of the cosmetic industry. The suspended lipid particles of this class, incidentally, are desired to have a limited average particle diameter and a predetermine or limited particle size distribution.

In response to the desire to attain uniform sizing of these lipid particles, methods such as are cited below are adopted for finely dividing and uniformly sizing the aforementioned suspended lipid particles: (a) A method of production of finely divided lipid particles which effects fine division and uniform sizing of lipid particles by making use of the mechanical shear strength, such as of a high pressure homogenizer (American Biotechnology Laboratory, volume 3, P. 36 to 41, 1985), and (b) a method of production of finely divided lipid particles which attains fine division and uniform sizing of lipid particles by forcing the lipid particles through a filtering device or a filter by exertion of a pressure in the range of 1 to 7 kgf/cm$^2$.

The expression "method for production of suspended lipid particles", as used herein, means the act of finely dividing and uniformly sizing the lipid particles in the suspended lipid particles produced, in advance or prior to finely dividing and uniformly sizing the lipid particles as described above. The aforementioned emulsions and liposomes are cited as representing the suspended lipid particles which answer the description given above. These suspended lipid particles are prepared by using phospholipid, such as lecithins and sphingomyelins; lipids such as cholesterol, dicetyl phosphate, diglycerides, triglycerides, and tocopherols; glycolipids, such as gangliosides; nonionic surfactants, such as polyoxyethylene sorbitan fatty acid esters and polyethylene glycol fatty acid esters; and ionic surfactants such as sodium lauryl sulfate, as raw materials. Specifically, they are water-soluble drugs, lipid-soluble drugs, and oil-soluble drugs, for example.

The aforementioned methods for production of finely divided lipid particles, however, are each at a disadvantage in terms of feasibility as follows. In the case of the method described in (a) above, the great shear strength severs or degenerates part of such macromolecular drugs substances as peptides and proteins. The intense heat which results, even if partially applied, induces decomposition of drug substances which are vulnerable to heat. This method is further handicapped by the fact that accurate control of particle diameter is extremely difficult because mechanical force must be relied on for the fine division of the lipid.

In the case of the method described in (b) above, the actual practice of this method is such that the fine division of the suspended lipid particles cannot be carried out efficiently on a mass production scale due to the selection of the kind and construction of a filter such as, for example, a membrane filter, or due to the combination of the membrane filter so selected with a commercial scale, or due to the combination of selection of the kind and construction of a filter such as, for example, a membrane filter and a filter support serving the purpose of mechanically reinforcing and supporting the selected membrane filter. It may be added in this respect that the term "membrane filter" mentioned above, as used herein means what is obtained by irradiating a thin film of charged particles thereby inscribing tracks in the thin film and subjecting the tracks to a treatment for chemical corrosion thereby forming in the thin film innumerable cylindrical pores of a uniform diameter of the order of microns substantially perpendicularly to the surface of the thin film at a density, for example, of some hundreds of million pores per 1 cm$^2$. When this membrane filter is combined with a filter support and results in, oris otherwise vested consequently with, a mechanically reinforced structure, the available area of the membrane filter is decreased and the efficiency thereof in fine division and of the uniform sizing of suspended lipid particles is degraded.

Further, when the membrane filter is produced by swelling a macromolecular material with a solvent and drying the swelled material thereby furnishing the macromolecular material with reticularly distributed micro pores therein, the resultant filter is incapable of finely dividing and uniformly sizing the aforementioned suspended lipid particles by the method that involves forcing the suspension through the filter under pressure in the aforementioned range of 1 to 7 kgf/cm$^2$.

In any event, the method of (b) mentioned above is at an advantage with respect to the function of a filter medium in enabling the residue of filtration or filter cake deposited on the surface of thin film to be easily peeled to renew the surface and allow repeated service of the filter because filter the cake predominantly occurs on the surface of the film. It is, however, incapable of efficiently attaining necessary fine division of the suspended lipid particles on the scale of quantity production. To make the matter worse, since the filter support has a limited opening ratio, the filter support impedes the flow of suspended lipid particles which have been reduced in size by being forced through the micro pores in the membrane filter under pressure. As a result, this membrane filter prevents the necessary fine division from being efficiently attained on a mass production scale.

Incidentally, since the membrane filter is in the form of a thin film, it is put to use as supported with a supporting screen such as, for example, a flat metallic screen or a mesh screen formed of plain weave of mono-filaments, in other words in the form of a cassette or a unit.

When the membrane filter is applied closely to the supporting screen mentioned above in preparation for use, the membrane filter is degraded markedly in its capacity for filtration because the pores in the part of the membrane filter which adjoins the part of the supporting screen which is destitute or devoid of pores are closed. Alternately, in the case of a construction having a mesh screen of thin monofilaments of metal or resin interposed between the surface of a membrane filter and the surface of a supporting screen thereby separating the membrane filter and the supporting screen, the degradation of the membrane filter in the capacity for filtration can be precluded minimized or avoided. Particularly when the separation just mentioned is effected with a fine woven mesh screen, the efficiency of filtration is two to five times as high as when no separation is made.

When the membrane filter mentioned above is so constructed that the fine mesh screen of monofilaments is to be interposed between the surface of the membrane filter and that of the supporting screen each time the membrane filter is put to use as a filtering member, it entails a complicated handling which may not be considered practical. To cope with this problem, the idea of giving this membrane filter the shape of a cassette (for example) by nipping the membrane filter on the opposite main surfaces thereof between fine mesh screens identical in shape and size with the membrane filter and welding or fastening the peripheral edge part of the membrane filter, either alone or in combination with the peripheral part of a central hole forming a central concentrated flow path, with suitable resin in such a manner that the peripheral part(s) will be buried in the resin thereby ensuring unification and perfect sealing of the membrane filter, has been under test to determine feasibility thereof.

The adoption of the construction of a cassette described above allows ample elimination and preclusion of the complexity of actual use of the membrane filter. When the fine mesh screens identical in shape and size with the membrane filter are accurately adjoined to and superposed on the opposite main surfaces of the membrane filter and they are welded or fastened together with resin possessed of flexibility, a fair possibility ensues that the superposed layers will deviate from alignment or the membrane filter and the mesh screens will become loose or gather wrinkles. This construction, therefore, cannot be called satisfactory in terms of the yield of production of membrane filter cassettes and the reliability of function of the filter. For example, it is difficult to have the membrane filter and the mesh screens, which are relatively thin membranes or thin layers, accurately adjoined to each other in a thoroughly stretched state. Moreover, it is an extremely difficult task to keep the membrane filter and the mesh screens in a state producing neither wrinkle nor sag, and also to weld or fasten them in situ with flexible resin without inducing deviation or injury and attain unification and perfect sealing. The yield of production from the standpoint of outward appearance, for example, is only 40% at most. The yield of production in terms of the reliability of function (performance) is even less than 10% in consideration of the fact that membrane filter cassettes of this kind are generally put to use as superposed in a total of about 20 layers (about 100 layers at times).

Further, in the case of the method of (b) mentioned above, not only is there a problem inherent in the filter but also a device fitted with the membrane filter cassettes such as, for example, a filtering device has a problem of its own. Prerequisites for fine division and uniform sizing on, scale a mass production of the suspended lipid particles represented by emulsions and liposomes include ensuring that, (1) the sizing device is capable of being directly connected to a storage tank and capable of treating a large volume of the suspension of lipid particles at a time, (2) the sizing is preformed while excercising control of the temperature of the suspension of lipid particles under treatment to a temperature not lower than the phase transition temperature of the lipid, (3) the sizing is preformed while excercising control of the pressure of the reaction system so as to proceed in the presence of increased pressure, and (4) the sizing device exhibits a required ability to oppose corrosion when the lipid particles are intended for use in medicines (which are mostly weakly acidic or weakly basic).

The conventional filtering devices, however, do not fulfill the requirements (1) to (4) mentioned above.

As described above, membrane filter cassettes, membrane filter units, and methods and apparatus and for the production of suspended lipid particles which have been introduced to the art are not effective in ideally allowing fine division of suspended lipid particles and minimizing the range of particle diameter distribution (by uniform sizing). Thus, the desirability of developing a membrane filter cassette, a membrane filter unit, and a method and an apparatus for the production of suspended lipid particles which are capable of efficiently effecting fine division of suspended lipid particles with a minimization of the range of particle diameter distribution as by uniform sizing has been finding popular recognition.

SUMMARY OF THE INVENTION

The present invention, therefore, has an object of providing a filter unit which is suitable for effecting fine division of suspended lipid particles efficiently on a mass production scale.

This invention has another object of providing a high-pressure sizing apparatus which is suitable for effecting fine division (sizing, extrusion) of suspended lipid particles (emulsions, liposomes, etc.) efficiently on a mass production scale.

This invention has a further object of providing a method for the production of suspended lipid particles which is suitable for effecting fine division of suspended lipid particles with high efficiency on a mass production scale.

This invention has still another object of providing a method for the production of a membrane filter cassette for a filter unit which is suitable for effecting fine division of suspended lipid particles efficiently on a mass production scale.

The filter unit according with this invention includes comprising a plate made of a metal such as, for example, stainless steel and provided with stepped through holes opening with a larger diameter on one main surface side and with a smaller diameter on the other main surface side (providing the ratio of diameter of larger-diameter openings/ diameter of smaller-diameter openings is desired to be in the range of 1:0.01–0.5) or a pressureproof supporting plate provided on one main surface thereof with inclined liquid flow grooves arranged in a radial pattern and concentric circular liquid flow grooves adapted to intersect the radially arranged inclined liquid flow grooves and a membrane filter disposed on the larger-diameter opening surface of the porous supporting plate or on the surface of the pressureproof supporting plate containing the liquid flow grooves. The membrane filter mentioned above is provided with liquid flow paths in the form of micro pores piercing the filter in the direction of thickness thereof or liquid flow paths in the form of a fine reticular texture.

The high-pressure sizing apparatus according with this invention comprises a first pressureproof housing and a second pressureproof housing having mutually opposed opening surfaces adjoined to each other to form a sealed chamber, a filter unit internally disposed in the proximity of a sealing part of the sealed chamber formed jointly by the first pressureproof housing and the second pressureproof housing and adapted to partition the internal empty space of the sealed part into a first pressureproof housing area and a second pressureproof housing area, an inlet serving to introduce the substance for sizing under pressure of 8 kgf/cm$_2$ or higher and communicating with the first pressureproof housing area, an outlet serving to discharge the treated substance and communicating with the second pressureproof housing area, and temperature controlling means integrally disposed on the outer surface of the first pressureproof housing and adapted to control the temperature of the substance under treatment and in the process of being supplied, which high-pressure sizing apparatus is characterized by the fact that the filter unit comprises a support provided with stepped through holes opening with a larger diameter on one main surface side and with a smaller diameter on the other main surface side (providing that the ratio of diameter of larger-diameter openings/smaller-diameter openings is desired to be in the range of 1:0.01 to 0.5) or a pressureproof supporting plate provided on one main surface thereof with inclined liquid flow grooves arranged in a radial pattern and concentric circular liquid flow grooves adapted to intersect the radially arranged inclined liquid flow grooves and a membrane filter disposed on the larger-diameter opening surface of the porous plate or the surface of the pressureproof supporting plate containing the liquid flow grooves and provided with micro pores piercing the filter in the direction of thickness or with liquid flow paths distributed in the filter in a reticular pattern and has the membrane filter is set in place and disposed as the first pressureproof housing area side.

The apparatus can be employed at higher pressure over 8 kgf/cm$^2$ to extrude lipid particles through membrane filter(s) to result fine lipid particles such as liposomes, emulsions and etc.

The method for production of suspended lipid particles (e.g., liposomes, lipid, emulsions, etc) according with this invention is characterized by installing a filter unit comprising a supporting plate of a metal such as, for example, stainless steel provided with through holes opening with a larger diameter on one main surface side and with a smaller diameter on the other main surface side (providing the ratio of diameter of larger-diameter openings/smaller-diameter openings is desired to be in the range of 1:0.01 to 0.5) or a pressureproof supporting plate provided on one main surface thereof with inclined liquid flow grooves arranged in a radial pattern and concentric circular liquid flow grooves adapted to intersect the radially arranged inclined liquid flow grooves and a membrane filter disposed on the larger-diameter opening surface of the porous supporting plate or on the liquid flow groove-containing surface of the pressureproof supporting plate and provided with micro pores piercing the filter in the direction of thickness or with liquid flow grooves distributed in the filter in a reticular pattern, and supplying a suspension of lipid particles under pressure of 8 kgf/cm$_2$ or higher from the membrane filter side thereby effecting fine division of the liquid particles in the suspension by causing the suspension to pass through the micro pores piercing the membrane filter, the through holes in the supporting plate, or the liquid flow grooves.

The method for production of a membrane filter cassette according with this invention is characterized by comprising a step of superposing thermoplastic resin films one each through the medium of a mesh screen on the opposite main surfaces of a membrane filter, a step of thermally fusing selectively an edge part of the membrane filter and the corresponding area of the thermoplastic resin film thereby integrally welding the two thermoplastic resin films and forming a sealed part, and a step of cutting out the thermoplastic resin films inside the sealed part and exposing the membrane filter having the opposite main surfaces thereof nipped between the mesh screens.

These aspects of the present invention have been perfected on the basis of experiments which have demonstrated that the construction of a filter unit is realized by assembling a membrane filter provided with minute through holes perforated by irradiation with charged particles and chemical etching or a membrane filter provided with minute liquid flow grooves formed in the direction of thickness and distributed in the form of a reticular texture by the procedure of swelling with an organic solvent and drying the swelled web and a supporting plate provided with through holes or a pressureproof supporting plate having straight liquid flow grooves arranged in a radial pattern and concentric circular liquid flow grooves adapted to intersect the radially arranged liquid flow grooves and that lipid particles having a limited average particle diameter and a limited particle sized distribution are obtained easily with high repeatability by supplying a suspension of lipid particles under pressure and forcing this suspension through the filter unit.

BRIEF DESCRIPTION OF THE DRAWINGS

FIG. 3 shows examples of particle diameter distribution of lipid particles produced by the method of production of suspended lipid particles by the use of the filter unit illustrated in FIG. 1; (a) representing the diagram of particle diameter distribution of the suspended lipid particles prior to fine division and (b) the diagram of particle size diameter distribution of the suspended lipid particles subsequent to fine division.

FIG. 8 illustrates an example of the other construction of a pressureproof supporting plate to be used in the construction of a filter unit incorporated as a component part in the high-pressure sizing apparatus according with this invention, in (a) a flat view, (b) a cross-section, and (c) a partially magnified cross section.

FIG. 9 illustrates by way of model one mode of embodying one example of the production of a membrane filter cassette according with this invention, (a) representing a cross section depicting the state in which a membrane filter, mesh screens, and thermoplastic resin films are superposed, (b) a cross section depicting the state in which a sealed part is formed by thermally fusing selectively the thermoplastic resin films of the superposed layers, and (c) a cross section illustrating the state in which the thermoplastic resin films are selectively punched to give rise to a desired membrane filter cassette.

FIG. 10 illustrates by way of model one mode of embodying another example of the production of a membrane filter cassette according with this invention, (a) a cross section depicting the state in which a membrane filter, mesh screens, and thermoplastic resin films are superposed, (b) a cross section depicting the state in which the thermoplastic resin films of the superposed layers are thermally fused selectively to form a sealed part, and (c) a cross section depicting the state in which the thermoplastic resin films are selectively punched so as to give rise to a required membrane film cassette.

DETAILED DESCRIPTION OF THE INVENTION

Now, this invention will be described in detail below.

The membrane filter to be used in this invention comes in two types, i.e. one type provided with micro pores piercing the filter in the direction of the thickness of the filter and the other type provided with minute liquid flow paths formed similarly in the direction of thickness of the filter and distributed in the form of a reticular texture or network. The membrane filter which is provided with micro pores piercing the filter in the direction of thickness thereof contains such minute through pores in an opening ratio in the approximate range of about 0.1% to about 18%. The membrane filters which are effectively usable herein include membrane filter made of such materials as films selected from a group consisting of polycarbonate film, polyester film, polysulfone film, polyethylene film, and polypropylene film and provided with micro pores formed by irradiation with charged particles and chemical etching in the direction of thickness, and those made of the same materials as mentioned above and provided with micro pores perforated for example by some other means in the direction of thickness. These micro pores have diameters in the range of about 0.010 to about 14 µm, preferably in the range of about 0.015 to about 3 µm, and more preferably in the range of about 0.1 to about 1 µm and it is preferred that these micro pores be distributed as uniformly as possible.

The membrane filter which is provided with minute liquid flow paths formed in the direction of thickness and distributed in the form of a reticular texture or network (resembling a sponge) has an average pore diameter of not more than about 1.0 µm, preferably not more than about 0.45 µm, and more preferably not more than about 0.22 µm. The membrane filters fitting this description include those which use substrates for example, selected from a group of substrates consisting of cellulose esters, polyvinylidene difluoride, glass fibers, acrylic acid copolymers, polytetrafluoroethylene, nylons (polyamides), and HT-Taflin. The membrane filters which are provided with minute liquid flow paths formed in the direction of thickness thereof and distributed in the form of a reticular texture or network are capable of not only effecting fine division and uniform sizing of suspended lipid particles (essentially under pressure of not less than 8 kgf/cm$^2$), but also sterilizing a drug substance under treatment.

When the supporting plate of the membrane filter mentioned above is a supporting plate provided with stepped through holes, for example, the diameter of the larger-diameter openings and that of the smaller-diameter openings are desired to be so selected and set or predetermined that the smaller diameter falls in the range of about 0.01 to about 0.5, based on the larger diameter taken as 1. This ratio of diameters, however, is not critical. The reason for this specific range is that the membrane filter has an inclination or tendency to fail to secure a sufficient area for the micro pores effectively. In the case of the plate provided with the stepped through holes, the opening ratio of the larger-diameter openings is in the approximate range of about 30% to about 90%, preferably in the range of about 60% to 70%. The thickness of this supporting plate may be generally in the approximate range of about 0.1 mm. to about 5 mm. The supporting plate for supporting the support provided with the stepped through holes is required to enough possess mechanical strength to withstand the pressure to be exerted to the substance under treatment (the suspension of lipid particles) and, therefore, is preferable reinforced and supported with a suitable material. Preferably the supporting plate is made of stainless steel of the grade of stainless steel 316 or stainless steel 316L, or a composite material using a core of iron and a coat or coatins of such a plastic material as tetrafluoroethylene resin, or glass. The thickness of taking into this supporting plate, though selected and set or predetermined consideration the size and shape of the support, is generally in the approximate range of 3 mm to 10 mm. The supporting plate, as described above, is preferably provided with stepped through holes, or orifices from the standpoint of smoothness with which the substance under treatment passes the plate. Alternatively, the through holes may be in a tapered shape having a diameter varied continuously in the direction of depth.

In the place of the support provided with the stepped through holes or even the pressureproof supporting plate formed of supporting plates, a pressureproof supporting plate may be used which is provided on the main surface thereof with inclined liquid flow grooves arranged in a radial pattern and concentric circular liquid flow grooves adapted to intersect the radially arranged liquid flow grooves. Again, in this case, the material and size of the supporting plate and the degree of inclination of the radially arranged liquid flow grooves are selected and set suitably depending on the size of the filter unit to be incorporated as a component part and the magnitude of the pressure exerted on the substance under treatment (suspension of lipid particles). When this pressureproof supporting plate is made of a plastic substance such as, for example, polycarbonate resin, the diameter thereof is about 290 mm and the thickness thereof is in the approximate range of 5 mm to 20 mm. When this supporting plate is made of stainless steel, the diameter thereof is about 290 mm and the thickness thereof is in the approximate range of 5 mm to 20 mm.

The liquid flow grooves which are arranged in a radial pattern are so inclined as to have a depth of about 0.8 mm on the outer side and a depth of about 4.8 mm on the inner side, respectively, of the supporting plate. They are circumferentially spaced with a narrower pitch on the inner side than on the outer side. This particular construction is not critical to the liquid flow grooves under discussion. These radially arranged liquid flow grooves, for example, may be increased in number on the outer side and joined by way of confluence to those of a smaller number on the inner side. Further, the concentric circular liquid flow grooves which are disposed so as to intersect the radially arranged inclined liquid flow grooves fulfill the role of interconnecting the adjacent radially arranged liquid flow grooves and, at the same time fulfill the role of, securing an available area for the membrane filter. The pitch at which the concentric circular liquid flow grooves are spaced and the depth of these grooves may be suitably selected and set or predetermined in accordance with the purpose of use and the capacity of operation.

In accordance with the present invention, the first pressureproof housing and the second pressureproof housing which jointly form the high-pressure sizing apparatus are made of stainless steel of the grade of stainless steel 316 or stainless steel 316L, or a composite material using a core member of iron and a coat or coating of such a plastic substance as tetrafluoroethylene resin (marketed under trademark designation of "Teflon"), or glass. These housings are invariably required to possess an ability to oppose resistance. The thickness of these housings is selected and set or predetermined with due consideration to the size and shape of these housings. The thickness of the first pressureproof housing, through depending on the pressure to be exerted on the substance under treatment which is supplied under pressure, is in the approximate range of 3 mm to 10 mm, for example, when the filter unit disposed internally in the high-pressure sizing apparatus has a diameter of about 90 mm. This thickness is in the approximate range of 3 mm to 60 mm when the diameter of the filter unit is about 290 mm. The temperature controlling means which is integrally disposed on the outer surface of the first pressureproof housing and adapted to control the temperature of the substance under treatment (the suspension of lipid particles) being supplied to the high-pressure sizing apparatus may be constructed so as to allow passage therethrough of hot and cold liquid media or permit adjustment of temperature with an electric heater.

Further, in accordance with the present invention, the pressure exerted on the suspension of lipid particles for the purpose of effecting fine division and homogeneous sizing of the lipid particles preferably, if not critically, has the lower limit thereof set at about 2 kgf/cm$^2$, preferably at about 5 kgf/cm$^2$.

When the membrane filter to be used is of the type provided with minute liquid flow paths arranged in the form of a reticular texture or network, the lower limit of the pressure to be used for the supply of the substance for sizing must be set at about 8 kgf/cm$^2$ or higher, preferably at about 10 kgf/cm$^2$ or higher, and more preferably at about 15 kgf/cm$^2$ or higher.

The filter unit of the present invention relies for mechanical reinforcement and support on a supporting plate provided with through holes, or orifices, which open or have openings with a larger diameter in one main or major surface and with a smaller diameter in the other main or major surface. It otherwise relies for mechanical reinforcement and support on a pressureproof supporting plate provided on one main or major surface thereof or inclined liquid flow grooves arranged in a radial pattern and concentric circular liquid flow grooves adapted to intersect the radially arranged liquid flow grooves.

Since the membrane filter is disposed on the one main or major surface side of the supporting plate which contains larger-diameter openings or on the surface side of the pressureproof supporting plate which contains the liquid flow grooves, it is allowed to assume a relatively large area destined to remain out of contact with the substance under treatment. Further, this membrane filter amply secures minute through pores or minute reticularly distributed liquid flow paths which are invariably pervious to lipid particles (hence an improvement in the available opening ratio).

The other main or major surface side of the support in which the through holes, or orifices, open with a smaller diameter is supported mechanically enough stability to oppose pressure by a supporting plate disposed on the surface side mentioned above and provided with through holes, or orifices distributed in a dispersed state therein. When the filter unit constructed as described above is put to use, it enables the suspension of lipid particles to be supplied thereto from the membrane filter side. By thus causing the suspension to pass through the minute through holes, or orifices or the minute liquid flow paths distributed in a reticular pattern in the membrane filter, the lipid particles in the suspension can be efficiently divided finely and the product of fine division can be recovered in highly satisfactory yield.

Further, in the case of the high-pressure sizing apparatus according with this invention, the supporting plate which contributes to furnish mechanical support to the membrane filter is provided, as described above, with through holes, or orifices opening with a larger diameter on one main or major surface and with a smaller diameter on the other main or major surface, or with inclined liquid flow grooves arranged in a radial pattern and concentric circular liquid flow grooves adapted to intersect the radially arranged liquid flow grooves. Since the membrane filter is disposed on the one main or major surface side of the supporting plate in which the minute through holes, or orifices, open with a larger diameter or on the surface side of the pressureproof supporting plate in which the liquid flow grooves are formed, it is allowed to assume a relatively large area destined to remain out of contact with the substance under treatment. The support provided with the through holes, or orifices, is stably supported mechanically enough to oppose pressure by causing the supporting plate having through holes, or orifices, dispersed therein to be disposed on the other main surface side of the porous member in which the through holes, or orifices, open with a smaller diameter.

The first housing, and the second housing which constitute by themselves the other part of the high-pressure sizing apparatus, are both constructed to oppose pressure and are provided with means to maintain the substance under treatment at a proper treating temperature. As a result, the suspension of lipid particles is enabled to be supplied under pressure from the membrane filter side of the filter unit constructed as described above. The fine division and uniform sizing of the lipid particles in the suspension, therefore, is attained with high efficiency by causing the suspension to pass under pressure through the minute through holes, or orifices, or the reticularly distributed minute liquid flow paths which are formed in the membrane filter. In the process of fine division and uniform sizing of the lipid particles owing to the aforementioned passage under pressure, since the temperature of the suspension under treatment and the temperature of the treating conditions are adjusted and retained properly, the fine division and uniform sizing is accomplished in an extremely efficient manner for and the product of the operation is attained in an unusually high yield.

Particularly when the membrane filter is provided with minute through pores or filter of a fixed diameter which are formed by irradiation with charged particles and chemical etching, the passage of the suspension of lipid particles through this membrane filter under pressure enables the lipid particles in the suspension to be easily divided finely to a fixed average particle diameter with a limited particle size distribution.

Further, in the method for production of the membrane filter cassette according with this invention, mesh screens and thermoplastic resin films are superposed one, each on the opposite main of major surfaces of the membrane filter, and the areas of thermoplastic resin film which correspond to the edge part of the membrane filter are thermally fused selectively. Since the superposed layers are integrated and allowed to form a sealed part as a result of the partial thermal fusion of the thermoplastic resin films on the opposite sides of the membrane filter, the integration is attained with minimal possibility of the superposed layers deviating separating from one another. The removal of the thermoplastic resin films inside the sealed part which has been formed by the integration mentioned above can be attained without inflicting damage to the mesh screens because the thermoplastic resin films are substantially completely separated from the mesh screens in the area outside the sealed part. As a result, the cassette which is so constructed as to expose the membrane filter having the opposite main surfaces thereof nipped between mesh screens can be easily produced in high yield. In other words extremely reliable, membrane filter cassettes can be produced with minimal defects in highly desirable yield without requiring complicated procedures or entailing any degradation of the function of filter.

EXAMPLE 1

First, a working example of the filter unit according with the present invention will be described below.

Figure 1:
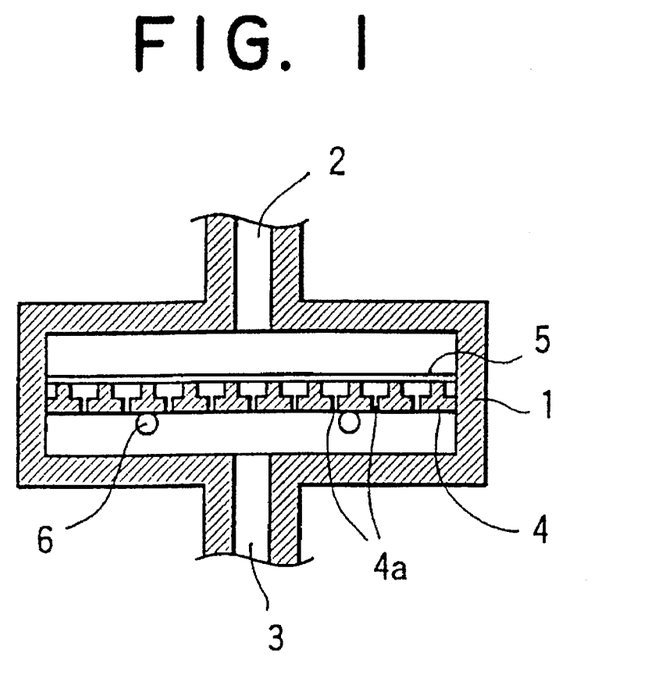
FIG. 1 is a cross section illustrating one example of the construction of the essential part of a filter unit according with the present invention.

FIG. 1 is a cross section illustrating one example of a filter unit, and an essential part of a (simplified) high-pressure sizing apparatus. In this diagram, 1 shown as a housing, provided with an inlet 2 for a suspension of lipid particles being supplied under pressure and an outlet 3 for extraction of the lipid particles which have undergone the treatment for fine division for a supporting plate 4 of stainless steel provided with stepped through holes or orifices 4a and set in place inside the housing 1; a membrane filter 5 disposed on the upper main surface of the supporting plate 4 in which the stepped through holes or orifices 4a open with a larger diameter, and a supporting plate 6 for mechanically reinforcing and supporting the supporting plate 4 is provided with the stepped through holes or orifices 4a, Though the filter unit is desired to incorporate this supporting plate for the reinforcing and supporting purposes mentioned above, from the practical this supporting plate may be omitted depending on the conditions under which the filter unit is used.

Figure 2:
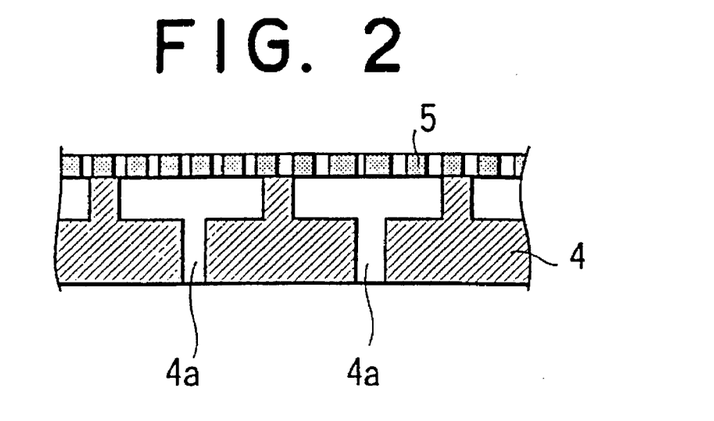
FIG. 2 is a cross section illustrating as magnified the construction of a membrane filter and a supporting plate containing stepped through holes as component parts of the filter unit according with the present invention and the layout of the component parts.

FIG. 2 is a cross section illustrating, in a magnified scale, the construction of a filter unit which is composed of the supporting plate 4 provided with the stepped through holes 4a and the membrane filter 5, namely the state in which the filter unit is assembled by having the membrane filter 5 superposed on the upper main surface of the supporting plate 4 in which the stepped through holes 4a open with a larger diameter.

In the construction of the filter unit described above, the supporting plate 4 provided with the stepped through holes 4a is a supporting plate of stainless steel having a thickness in the approximate range of 0.5 mm to 0.7 mm and provided with stepped through holes 4a opening with a larger diameter of about 0.85 mm in one main or major surface and with a smaller diameter of about 0.5 mm in the other main or major surface, with the openings of the larger diameter accounting for an opening ratio of about 65%. The membrane filter 5 is a product obtained by preparing a polycarbonate film having a thickness in the approximate range of 6 µm to 20 µm, irradiating this polycarbonate film with charged particles, and thereafter selectively etching the film with an alkali solution such as NaOH thereby imparting minute through pores or orifices of a diameter of about 0.2

µm thereto. The opening ratio of this membrane filter 5 is approximately of 20% when the minute through pores or orifices have a diameter of about 0.2 µm. The supporting plate 6 mentioned above is a product obtained by preparing a stainless steel plate having a thickness of 4 mm and boring (chamfered) through holes or orifices having a diameter of 4 mm as spaced substantially equidistantly circumferentially on concentric circles spaced radially at an interval of 21 mm. It may be produced in some other construction.

EXAMPLE 2

Here, an example of the production (uniform sizing) of given suspended lipid particles by the use of an apparatus constructed by setting the filter unit constructed as described in Example 1 within the housing 1. The particle diameter and the particle size distribution of lipid particles in liposomal suspension were determined with a particle size analyzer (produced by Particle Sizing System Corp. and marketed under trademark designation of "Nycomp 370 Series").

Figure 3A:
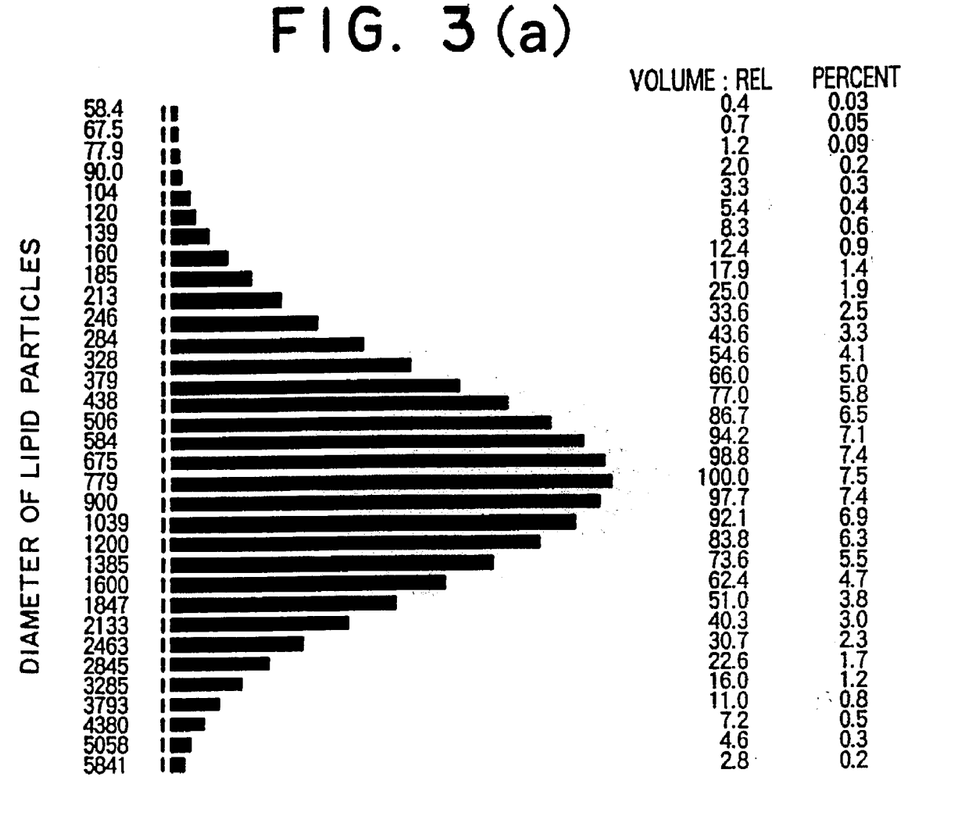

First, egg yolk lecithin, cholesterol, and egg yolk phosphatidylglycerol weighed out in the respective amounts of 10 mM, 8 mM, and 2 mM were placed in a vessel made of glass. To the glass vessel, a mixed liquid consisting of chloroform and methyl alcohol in a volumetric ratio of 5:1 was added to solubilize the mixture and nitrogen gas was blown in to remove the organic solvent. Then, the resultant mixture and 2 liters of an aqueous 9% saccharose solution added thereto were stirred together with a homomixer to prepare a liposomal suspension. FIG. 3 (a) shows the particle size distribution of the liposomal suspension prepared as described above. Then, two liters of the liposomal suspension (suspension for treatment) was injected via the inlet 2 with a pressure of about 20 kgf/cm$^2$ into the apparatus constructed by setting the aforementioned stepped filter in the housing 1 and finely divided by being passed through minute through pores (0.2 µm in diameter) formed in the filter unit set and supported inside the housing 1 of the aforementioned apparatus, namely the membrane filter 5 disposed on the surface of the supporting plate 4 of stainless steel in which the stepped through holes 4a open with a larger diameter. The suspension now containing finely divided liposomes was passed through the stepped through holes 4a of the plate 4 and recovered via the outlet 3.

Figure 3B:
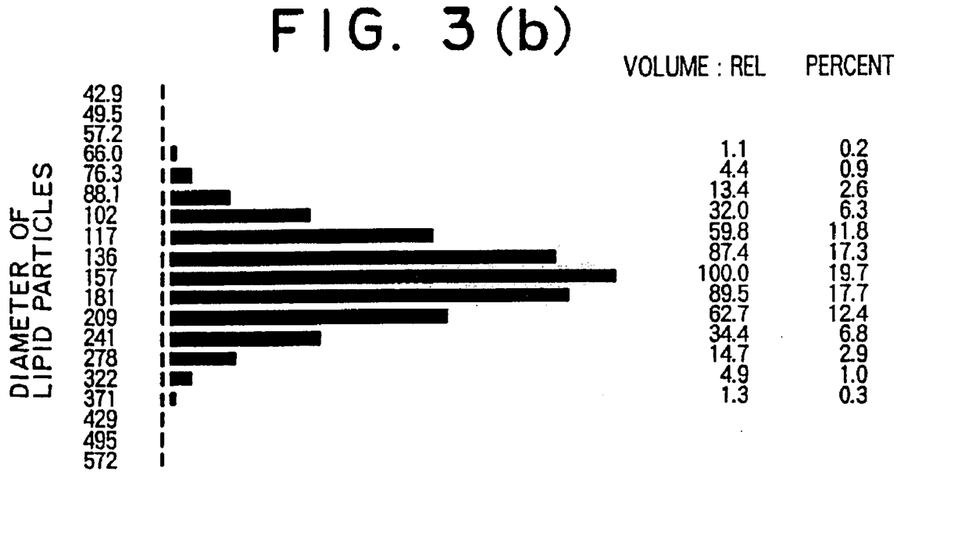

The procedure for fine division described above was repeated once more. The particle diameter and the particle size distribution of the lipid particles in the liposomal suspension resulting from the repeated procedure were determined. From the results of this determination depicted in FIG. 3 (b), it is clearly shown that the liposomal suspension had a definite average particle diameter and a specific particle size distribution both conceivably fit for such medicines as, for example anti-tumor drugs and anti-AIDS drugs. The volume of lipid recovered via the outlet 3 was 99.2% of the volume injected via the inlet 2, a fact indicating that substantially all the lipid was recovered.

The present example demonstrates that in the method for production of finely divided lipid from the liposomal suspension, the minute through pores in the membrane filter 5 were not clogged, the membrane filter 5 was not damaged in any respect, the suspended lipid particles resulting from the treatment for fine division flowed freely without being obstructed in any manner by the supporting plate 4, and they could be easily and efficiently passed through the stepped through holes 4a in the supporting plate 4 and recovered via the outlet 3 of the apparatus proper 1.

Figure 8A:
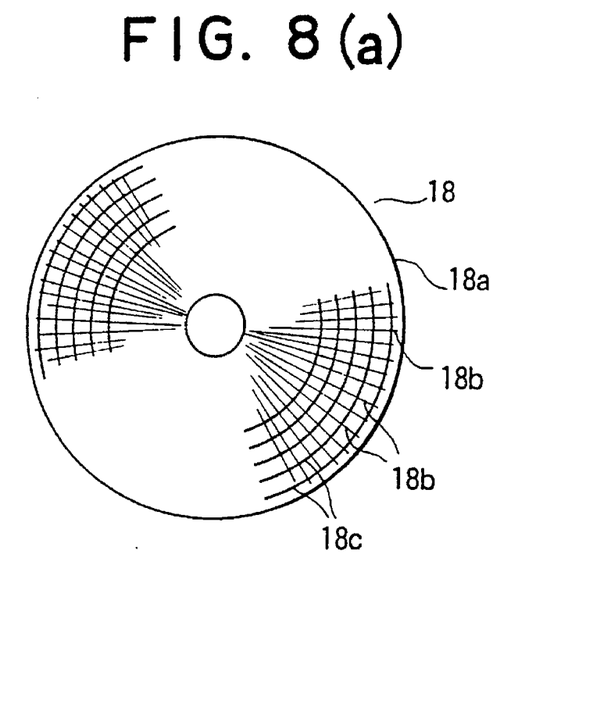
Figure 8B:
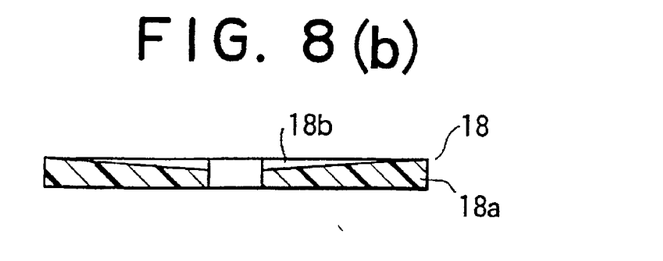
Figure 8C:
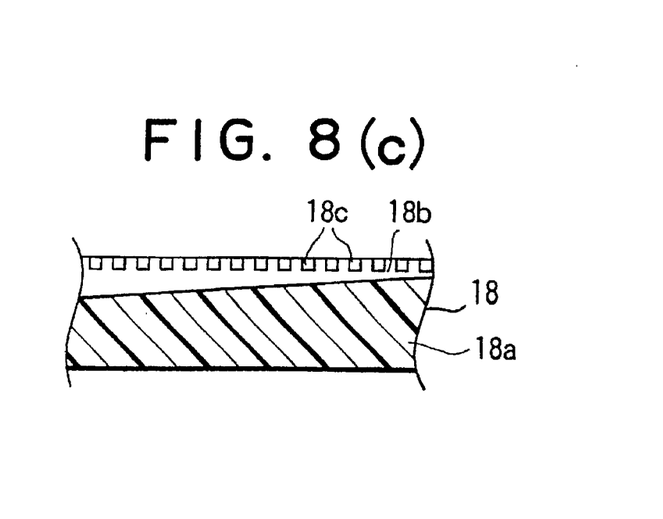

In this example, the same results as described above were obtained even when the suspended lipid particles were changed and the pressure used during the supply of suspended lipid particles under pressure was changed to 5 kgf/cm$^2$, 10 kgf/cm$^2$, 15 kgf/cm$^2$, 20 kgf/cm$^2$, 25 kgf/cm$^2$, 30 kgf/cm$^2$, or 35 kgf/cm$^2$. The same results as shown above can be obtained when the pressure used for the forced supply is changed to 40 kgf/cm$^2$. The results were substantially the same when the filter unit was constructed by having the membrane filter 5 nipped on the opposite surfaces thereof between the mesh screen and disposed on the supporting plate 4 provided with stepped through holes 4a as when the filter unit was constructed by having the membrane filter 5 disposed on one main surface of the supporting plate on which the supporting plate was provided with inclined liquid flow grooves arranged in a radial pattern and concentric circular liquid flow grooves adapted to intersect the radially arranged liquid flow grooves [FIG. 8 (a) to (c)].

It is clearly noted from Example 1 and Example 2, cited above, that the filter unit according with this invention and the method for production of suspended lipid particles by the use of this filter unit permit easy mass production of suspended lipid particles having a definite average particle diameter and a specific particle size distribution and, when applied pharmacologically to anti-tumor drugs or anti-AIDS drugs, applied to the food industry, or applied to the cosmetic industry, bring about many advantages from the practical point of view.

EXAMPLE 3

Figure 4:
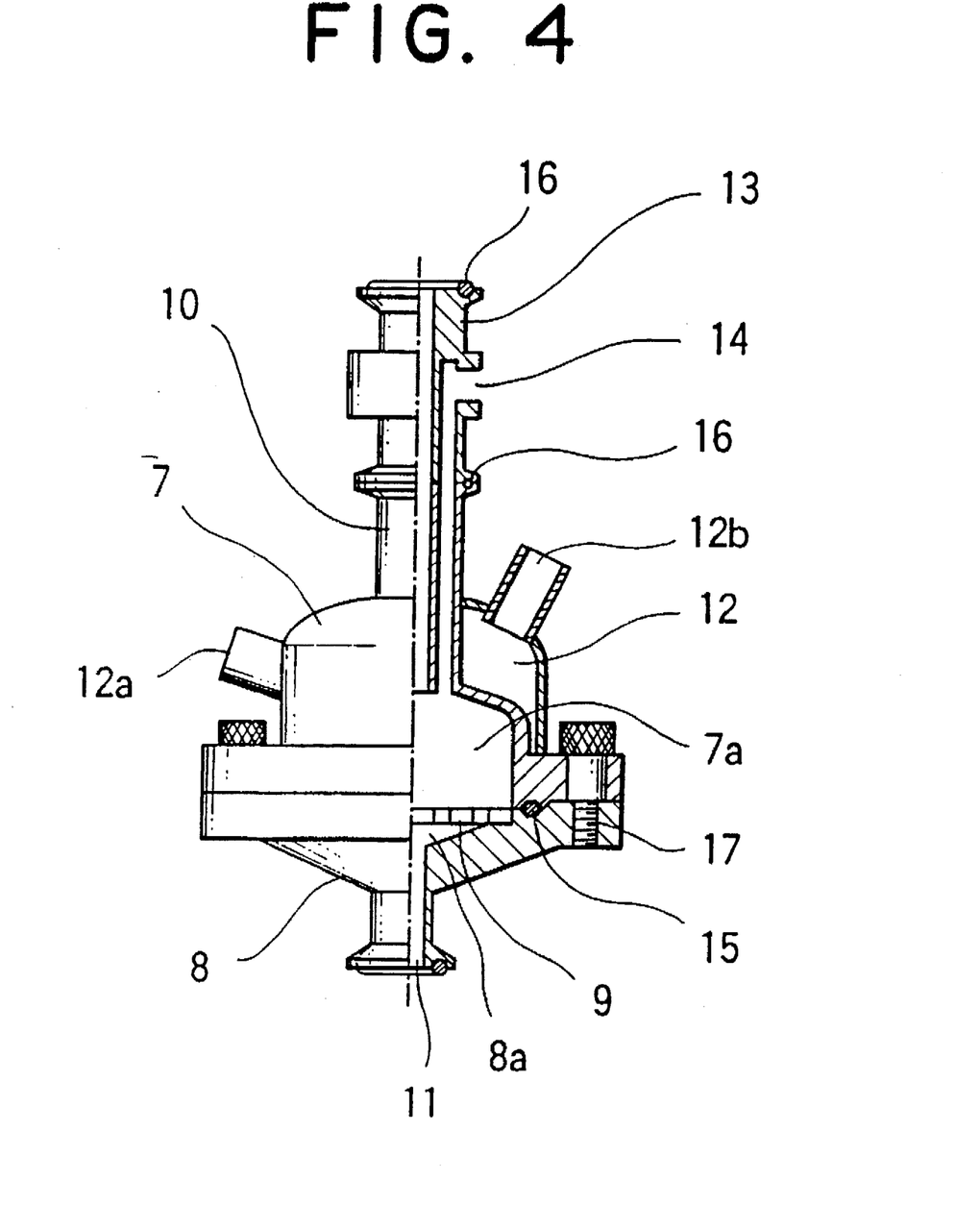
FIG. 4 is a partial cutaway cross section illustrating an example of the construction of the essential part of a high-pressure sizing apparatus according with this invention.
Figure 5:
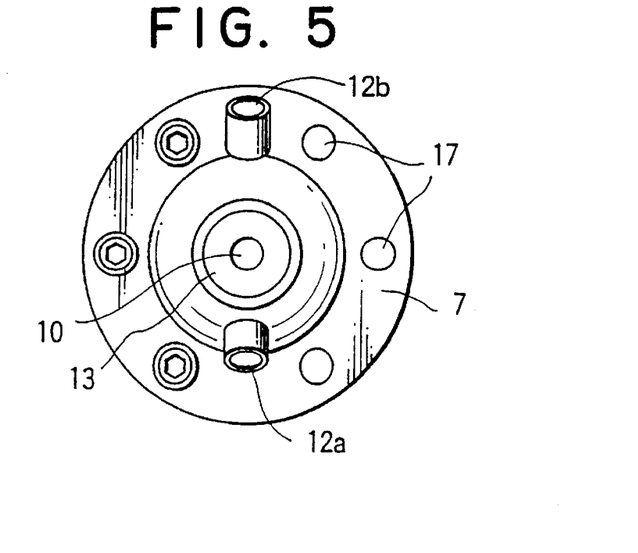
FIG. 5 is a top view illustrating one example of the construction of the high-pressure sizing apparatus according with this invention.

FIG. 4 and FIG. 5 illustrate one example of the construction of the essential part of a high-pressure sizing apparatus according with this invention respectively in a partially cutaway cross section and in a top view.

First in the diagrams, 7 and 8 stand respectively for a first pressureproof housing 7 and a second pressureproof housing 8 which jointly form a sealed member by having their opposed open surfaces brought into close contact, a filter unit 9 set in place in the proximity of the sealing part of the sealed part jointly formed by the first pressureproof housing 7 and the second pressureproof housing 8, and adapted to partition the inner empty space of the sealed part into a first pressureproof housing area 7a and a second pressureproof housing area 8a an inlet 10 communicating with the first pressureproof housing area 7a partitioned by the filter unit 9 and serving to introduce under pressure the substance undergoing treatment, and an outlet 11 communicating with the second pressureproof housing area 8a partitioned by the filter unit 9 and serving to discharge the substance which has been treated. In the high-pressure sizing apparatus described above, the inlet 10 for introducing under pressure the substance undergoing treatment is connected to a storage tank for the substance undergoing treatment such as a suspension of lipid particles, and the outlet 11 for discharge of the treated substance is connected to a storage tank for the product of fine division and uniform sizing.

Then, 12 stands for temperature controlling means disposed integrally on the outer surface of the fist pressureproof housing 7 and adapted to control the temperature of the substance being supplied for treatment. The temperature controlling means, for example, is a medium flow path adapted to permit selective flow of a hot medium or a cold medium and disposed and formed integrally. Here, the medium flow path (temperature controlling means) 12 admits the heat medium via a medium inlet 12a, uses it in the control of temperature of the outer surface of the first pressureproof housing 7 and the interior of the first pressureproof housing area 7a, and discharges the used heat medium via an outlet 12b.

FIG. 4, shows a connecting pipe 13 continuing into the inlet 10 for admitting the substance for sizing under pressure, an air vent 14 formed along the wall part of the inlet 10 and the wall part of the connecting pipe 13, a packing 15 disposed in a sealing surface formed by contact of the opening surface of the first pressureproof housing 7 and the opening surface of the second pressureproof housing 8, a packing 16 disposed in a connecting part such as connecting pipe 13, and a clamping bolt 17 for integrating the first pressureproof housing 7 and the second pressureproof housing 8.

Figure 6:
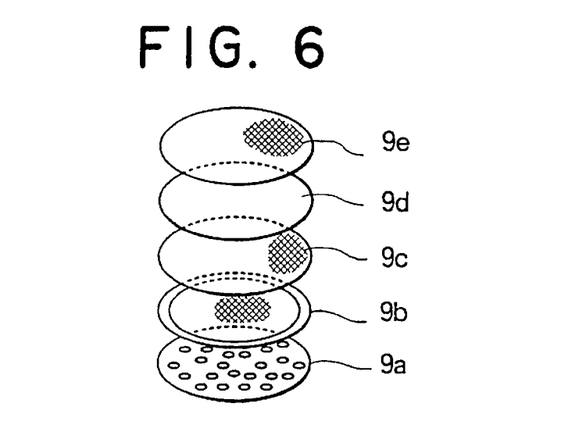
FIG. 6 is an exploded view illustrating one example of the construction of a filter unit incorporated as a component part in the high-pressure sizing apparatus according with this invention.
Figure 7:
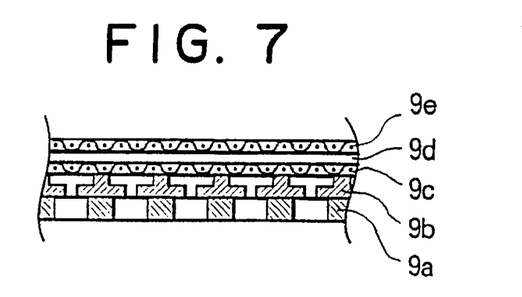
FIG. 7 is a cross section illustrating one example of the construction of the essential part of a filter unit incorporated as a component part in the high-pressure sizing apparatus according with this invention.

Now, the construction of the filter unit 9 will be described below with reference to FIG. 6 and FIG. 7. FIG. 6 is an exploded view illustrating an example of the construction of the essential part of the filter unit 9 mentioned above and FIG. 7 is a cross section illustrating an example of the construction of the same essential part. The filter unit 9 is composed of a pressureproof supporting plate 9a having through holes formed therein in a dispersed state, a support 9b made of stainless steel, supported on the pressureproof supporting plate 9a, and provided with stepped through holes or orifices opening with a larger diameter on one main or major surface and with a smaller diameter on the other main or orifices surface (providing a ratio of diameter of larger-diameter openings/diameter of smaller-diameter openings preferably in the range of 1:0.01 to 0.5), a mesh screen 9c disposed on the larger-diameter opening side of the support 9b, a membrane filter 9d disposed on the support 9b through the medium of the mesh screen 9c and provided with micro pores pierced therein in the direction of thickness, and a mesh screen 9e disposed on the surface of the membrane filter 9d. This filter unit 9 has a side of the membrane filter 9d attached and disposed as the first side of pressureproof housing area 7a.

In the construction of the filter unit 9, described above, the support 9b provided with stepped through holes, or orifices, for example, is a support (plate) of stainless steel having a thickness in the approximate range of 0.5 mm to 0.7 mm and provided with stepped through holes, or orifices, opening with a larger diameter of about 0.85 mm in one main or major surface and with a smaller diameter of about 0.5 mm in the other main or major surface, with the larger-diameter openings contained in an opening ratio of about 65%. The membrane filter 9d is a product obtained by preparing a polycarbonate film of a thickness in the approximate range of 6 μm to 20 μm, irradiating the polycarbonate film with charged particles, and then selectively etching this film with an alkali solution such as, for example, NaOH thereby imparting thereto minute through pores of a diameter about of 0.2 μm. The opening ratio in this membrane filter 9d about 10% when the minute through pores mentioned above have a diameter of about 0.2 μm. The supporting plate 9a is a product obtained by having (chamfered) through holes of a diameter of 4 mm formed in a stainless steel plate of a thickness of 4 mm, for example, as circumferentially spaced substantially equidistantly on concentric circles spaced radially at an interval of about 21 mm. The porous supporting plate may be produced in some other construction when necessary. In this construction, the membrane filter 9d is nipped on the opposite surfaces thereof between the mesh screens 9c and 9e for the sake of protecting the membrane filter 9d. Depending on the conditions under which the filter unit 9 is used, these mesh screens 9c and 9e may be omitted.

A second high-pressure sizing apparatus similar in construction to the high-pressure sizing apparatus was produced by, using in the place of the membrane filter 9d of the membrane filter unit 9, a cellulose ester film or polyvinylidene difluoride film measuring 100 µm to 150 µm in thickness and containing minute reticularly distributed liquid flow paths of an average diameter of 0.22 µm.

EXAMPLE 4

This example concerns a method for the production (uniform sizing) of suspended lipid particles by fine division of the lipid particles in the suspension by the use of the high-pressure sizing apparatus constructed as described in Example 3 above. The liposomal suspension used in this experiment was prepared under the same conditions as in the experiment of Example 2.

The volume i.e., 2 liters, of the suspension was injected via the inlet 10 with a pressure of about 20 kgf/cm$^2$ into the high-pressure9 sizing apparatus mentioned above. It was then finely divided and uniformly sized by being passed under pressure through the filter unit 9 set inside and supported by the apparatus, specifically the minute through pores (0.2 µm in diameter) formed in the membrane filter 9d disposed on the surface of the supporting plate 9b in which the through holes formed therein opened with a larger diameter. The suspension of finely divided and uniformly sized liposomes which emanated from the membrane filter 9d was passed through the through holes in the porous supporting plate 9b and the through holes in the supporting plate 3a and recovered via the outlet 11. In the process of fine division and uniform sizing mentioned above, hot water at 60° C. introduced via the medium inlet 12a was supplied to the temperature controlling means (the medium flow path) 12 of the high-pressure sizing apparatus and discharged via the medium outlet 12b to adjust the temperature of the lipid particles being finely divided and uniformly sized to a level of about 60° C., i.e. the phase transition temperature of the liposomal suspension, and effect the fine division and uniform sizing.

This procedure of fine division and uniform sizing was repeated once more. When the lipid particles of the liposomal suspension resulting from the repeated procedure were tested for average particle diameter and particle size distribution, they were found to have a peak particle size of about 150 nm and a particle size distribution in the approximate range of 70 nm to 300 nm. The data clearly indicate that the fine sizing produced lipid particles which had a definite average particle size and a specific particle size distribution both fit for such medicines as for example anti-tumor drugs and anti AIDs drugs. The volume of lipid recovered via the outlet 11 was 99.2% of the volume, admitted via the inlet 10, a fact indicating that the lipid could be recovered substantially wholly.

In this example, when the magnitude of the pressure used in supplying suspended lipid particles as a substance for the treatment of fine division and uniform sizing was changed to 5 kgf/cm$^2$, 10 kgf/cm$^2$, 15 kgf/cm$^2$, 20 kgf/cm$^2$, 25 kgf/cm$^2$, 30 kgf/cm$^2$, or 35 kgf/cm$^2$, the results were substantially the same as in the experiment described above. Substantially the same results as shown above can be obtained when the pressure used for the forced supply is changed to 40 kgf/cm$^2$. The experiment described above represented a case of using suspended lipid particles as a substance for the treatment. The uniform sizing which was performed on other minute particles showed the same trend as observed in the experiment described above.

Further, in the filter unit 9, constructed as illustrated by example above, the operation and effect manifested thereby were not changed when a pressureproof supporting plate 18, constructed as illustrated in FIG. 8 (a), FIG. 8 (b), and FIG. 8 (c), respectively, in a plan view, in a cross section, and in a magnified cross section was used in the place of the pressureproof supporting plate 9a provided with through holes disposed in a dispersed state and the support 9b of stainless steel supported by the pressureproof supporting plate 9a and provided with through holes opening with a larger diameter in one main or major surface and with a smaller diameter on the other main or major surface. More specifically, a filter unit, which was obtained by preparing a circular polycarbonate resin plate having a diameter of about 90 mm and a thickness in the range of about 5 mm to about 20 mm, producing a pressureproof supporting plate 18 by inscribing, in one main or major surface of the circular polycarbonate resin plate 18a, first liquid flow grooves 18b inclined in the radial direction so that the grooves had a depth in the approximate range of about 0.1 mm to about 5 mm on the outer side of the plate and a depth in the approximate range of 1 mm to 15 mm on the inner side of the plate, and second liquid flow grooves 18c adapted to intersect the first liquid flow grooves 18b, and supporting, on the surface of the pressureproof supporting plate 18 containing the liquid flow grooves 18b and 18c, a membrane filter nipped on the opposite surfaces thereof between mesh screens, produced the same results as those obtained in the example cited above.

EXAMPLE 5

This example concerns a method for production of suspended lipid particles by the use of the second high-pressure sizing apparatus produced in Example 3 above.

First, L-α-dimyristoyl phosphatidyl glycerol (DMPG), egg yolk phosphatidyl choline, and cholesterol, weighed out in a molar ratio of 5.7:1.0:6.0, were placed in a vessel made of glass. The resultant mixture was solubilized with a small amount of chloroform and then blown with a stream of nitrogen gas to remove the organic solvent. Subsequently, the solubilized mixture was dried under a vacuum in a desiccator for one hour to attain thorough removal of the solvent. Then, a 9% aqueous sucrose solution was added to the drug mixture and it was homogenized by a homomixer, and untreated liposomal dispersion having a total lipid concentration of 34 mM was obtained. The lipid in the untreated liposomal dispersion had an average particle size of 517 nm. This untreated liposomal dispersion was divided into 100-ml portions and used for sizing.

The samples were severally injected through the inlet 10 under varying magnitudes of pressure of 10 kgf/cm$^2$, 12 kgf/cm$^2$, and 20 kgf/cm$^2$ into the second high-pressure sizing apparatus mentioned above and passed through the minute through pores or orifices of the membrane filter of the filter unit 9 internally supported in the sizing apparatus to be finely divided and uniformly sized. The liposomal suspension which had undergone fine division and uniform sizing was recovered through the outlet via the through holes, or orifices of the supporting plate 9b and the through holes or orifices of the supporting plate 9a. The results of this experiment are shown in Table 1. Virtually no residue remained on the filter during the fine division or during the uniform sizing.

TABLE 1

| Membrane filter made of | Pressure for supply, kgf/cm$^2$ | Recovery ratio of lipid, % | Average particle diameter, nm |
|---|---|---|---|
| Polyvinylidene difluoride | 20 | 97.9 | 222 |
|  | 15 | 97.6 | 236 |
| Cellulose-ester mixture | 12 | 96.8 | 216 |
| Cellulose-ester mixture | 10 | 97.3 | 190 |

For the purpose of comparison, in the apparatus using the membrane filter made of a cellulose-ester mixture, the same sample of untreated liposomal dispersion was injected through the inlet 10 in 7 kgf/cm$_2$ into the second high-pressure sizing apparatus and passed through minute reticularly dispersed liquid flow paths of the membrane filter of the filter unit 9 internally supported in the apparatus in an effort to attain fine division and uniform sizing. The dispersion obtained virtually no passage through the membrane filter and the liposomal dispersion did not attain desired fine division and uniform sizing.

EXAMPLE 6

Treatment of suspended lipid particles was carried out by repeating the procedure of Example 5, except that an untreated dispersion containing 5% of glucose (average lipid particle size of 517 nm) was used instead, to recover a suspension of finely divided and uniformly sized liposomes via the outlet 11. The results of this experiment are shown in Table 2. Virtually no residue remained on the filter during the fine division or during the uniform sizing.

TABLE 2

| Membrane filter made of | Pressure for supply, kgf/cm$^2$ | Recovery ratio of lipid, % | Average particle diameter, nm | Medication retention ratio, % |
|---|---|---|---|---|
| Polyvinylidene difluoride | 8 | 98.9 | 243 | 12.4 |
| Cellulose ester mixture | 8 | 100 | 285 | 14.0 |

It is clearly noted from Examples 3 to 6 that the high-pressure sizing apparatus according with this invention, and the method for production of suspended lipid particles by the use of the high-pressure sizing apparatus, allow easy mass production of lipid particles, uniformly sizing in a definite average particle size and a specific particle size distribution, and, when pharmacologically applied to such medicines as anti-tumor drugs and anti-AIDS drugs, or applied to the food industry or to the cosmetic industry, bring about many advantages from the practical point of view.

To be specific, since the high-pressure sizing apparatus according with this invention is provided with an inlet capable of being directly connected to a storage tank, it can treat the suspension of lipid particles in a large volume at a time. Since it is jacketed and consequently enabled to control temperature, it can control the temperature of the lipid under treatment to a level of not lower than the phase transition temperature of the lipid. Further, since it is vested with pressureproofness, it can perform the treatment in an atmosphere of increased pressure. The housings used in the apparatus are constructed with due consideration to corrosionproofness. Thus, the high-pressure sizing apparatus may well deserve to be regarded as highly effective means for uniformly sizing suspended lipid particles represented by emulsions and liposomes or for production of suspended lipid particles.

EXAMPLE 5

Figure 9A:
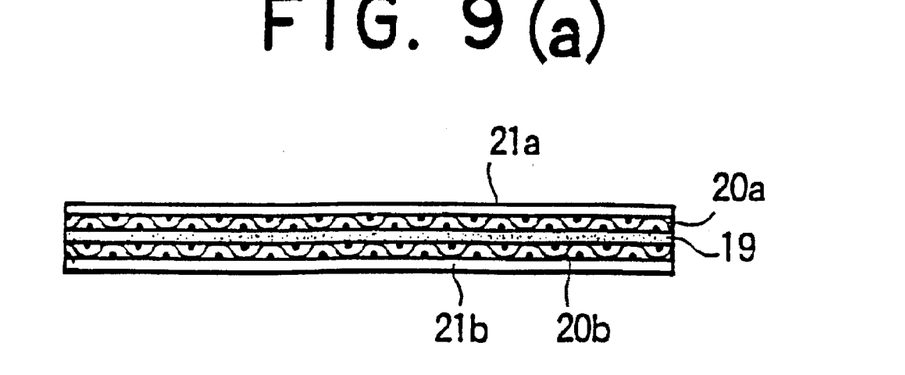
Figure 9B:
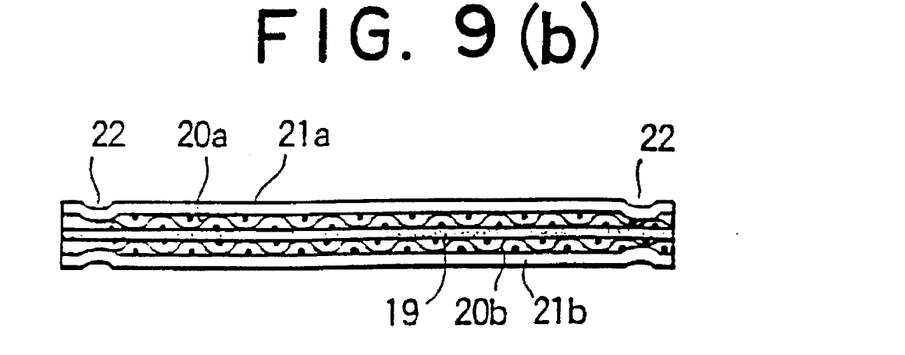
Figure 9C:
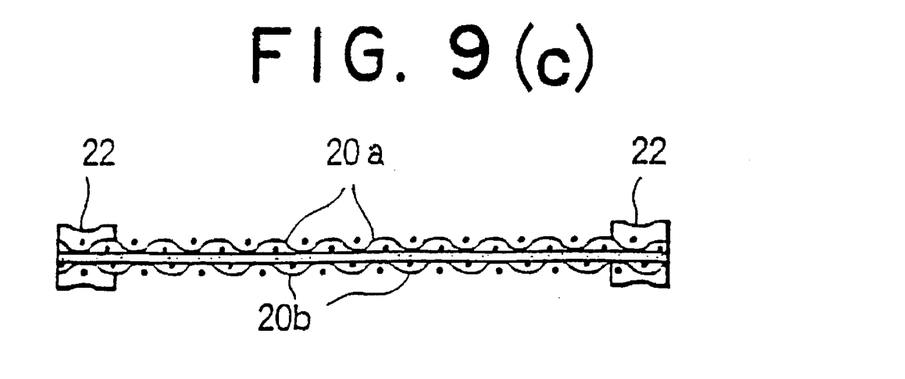

FIGS. 9 (a) to (c) illustrate, on a model, the manner of embodying an example of the production of a membrane filter cassette for use in a single layer disc type filtering device. First, mesh screens 20a and 20b of plain weave of monofilaments and thermoplastic resin films such as, for example, vinyl chloride resin sheets 21a and 21b were disposed as superposed one each on the opposite main or major surfaces of a membrane filter proper 19 [FIG. 9 (a)]. Then, the areas (edge parts) of the superposed vinyl chloride resin sheets 21a, and 21b, corresponding to the edge parts of the membrane filter 19, were selectively fused thermally to integrate the vinyl chloride resin sheets 21a and 21b and form a sealed part 22 [FIG. 9 (b)]. In the formation of the sealed part 22 by the selective thermal fusion, the integration could be obtained without inducing any positional deviation of the superposed layers.

After the sealed part 22 had been formed by the integration, as described above, the parts of the vinyl chloride resin sheets 21a and 21b enclosed with the sealed part 22 were cut off (by punching) to give rise to a membrane filter cassette of a construction having the opposite main or major surfaces of its own nipped between the mesh screens 20a and 20b, and the surfaces of the membrane filter 19 exposed and lending itself to the operation of a single layer disc type filtering device [FIG. 9 (c)]. In the selective removal by punching of the vinyl chloride resin sheets 21a and 21b, the impact of this punching inflicted no damage to the mesh screens 20a and 20b because the vinyl chloride resin sheets 21a and 21b are completely separated (liberated) from the surfaces of the mesh screen 20a and 20b in the area outside the sealed part 22.

When a total of 100 membrane filter cassettes were produced by repeating the procedure described above with necessary modifications, the membrane filter cassettes sustaining no visible breakage, warping, or sagging on the mesh screens 20a and 20b and enjoying safe quality were obtained in a yield of not less than 90%.

Figure 10:
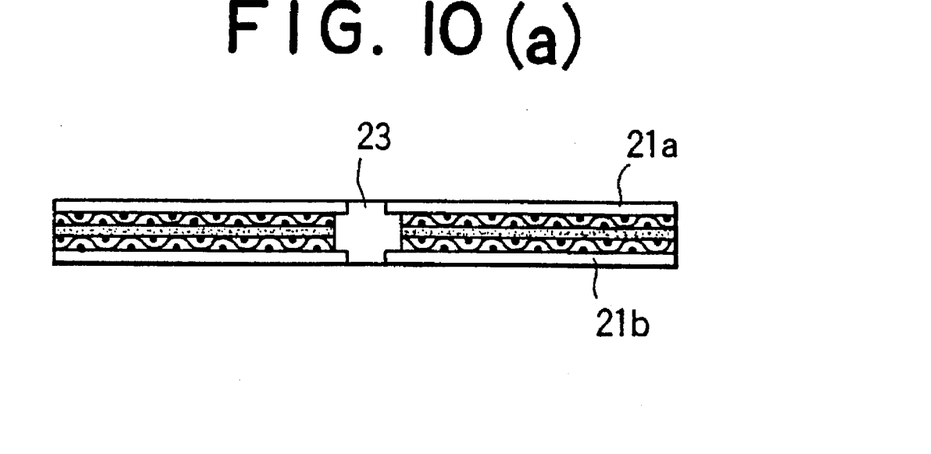

FIGS. 10 (a) to (c) illustrate, on a model, the manner of embodying one example of the production of a membrane filter cassette for use in a multilayer disc type filtering device. First, mesh screens 20a and 20b, and vinyl chloride resin sheets 21a and 21b were superposed one each on the opposite main or major surfaces of a membrane filter having formed in advance therein a central hole 23 destined to constitute itself a central concentric flow path [FIG. 10 (a)]. Then, the areas (inner edge parts) of the vinyl chloride resin sheets 21a and 21b, corresponding to the outer edge part and the inner edge part of the membrane filter 19, were selectively fused thermally to integrate by fusion the two vinyl chloride resin sheets 21a and 21b, and form sealed parts 22a and 22b [FIG. 10 (b)]. In the formation of the sealed parts 22a and 22b by the selective thermal fusion, the integration could be effected without inducing any positional deviation of the superposed layers. After the sealed parts 22a and 22b had been formed by the integration as described above, the circular parts of the vinyl chloride resin sheets 21a and 21b enclosed in the sealed parts 22a and 22b formed as described above were removed by punching to give rise to a membrane filter cassette having the opposite main or major surfaces of its own nipped between the mesh screens 20a and 20b and the surfaces of the membrane filter 19 exposed and lending itself to the operation of a multilayer disc type filtering device [FIG. 10 (c)]. In the case of this example of the production, similarly to the production of the cassette for use in the single layer disc type filtrating device described above, the produced cassette sustained no damage as in the mesh screens 20a and 20b.

When a total of 100 membrane filter cassettes were produced by following the procedure described above with necessary modifications, the membrane filter cassettes sustaining no visible breakage, warping, or sagging on the mesh screens 20a and 20b, and manifesting safe quality, were obtained in a yield not less than 90%. When a solution containing minute particles in a dispersed state was treated with a multilayer disc type filtering mechanism constructed by superposing 20 to 50 such membrane filter cassettes, the treatment produced an ideal result (outstanding effect of filtration). Though the membrane filter cassettes of this sort generally come in a circular shape two-dimensionally, they may be produced in an elliptical shape or a polygonal shape. As noted clearly from the description given thus far, the method for production of the membrane filter cassette enables the areas of thermoplastic resin films corresponding to the edge parts of the membrane filter in the superposed composite of membrane filter, mesh screens, and thermoplastic resin films to be selectively fused thermally and integrated to give rise to a sealed part and, meanwhile, enables the removal (by punching) of the parts of the thermoplastic resin films enclosed with the sealed part formed in as a result of the integration mentioned above to be effected easily without inflicting any damage on the mesh screens. In other words, the membrane filter cassette can be produced with minimal defects in a high yield without causing degradation of filter function or without requiring any complicated procedure.

What is claimed is:

1. A filter unit comprising:
   a supporting plate comprising orifices opening with a larger diameter in one surface and with a smaller diameter in another surface; and
   a membrane filter disposed on the surface of said supporting plate comprising openings with a larger diameter wherein said orifices in said supporting plate are stepped.

2. A filter unit according to claim 1, wherein said orifices have a diameter ratio of larger-diameter openings to smaller-diameter openings in a range of about 1:0.01 to about 1:0.5.

3. A filter unit according to claim 1, wherein said orifices of said supporting plate have an opening ratio, and said one surface provided with orifices opening with a larger diameter comprises a larger diameter opening side of said supporting plate, and the opening ratio on the larger-diameter openings side is in the range of about 30% to about 90%.

4. A filter unit according to claim 1, wherein said one surface comprises a main or major surface of said supporting plate, and said another surface comprises another main surface of said supporting plate.

5. A high-pressure sizing apparatus comprising:
   a sealed chamber comprising a first pressureproof housing comprising a sealing part and a second pressureproof housing comprising a sealing part, each said sealing part comprising an opposed surface in close contact;
   a filter unit set in an area proximate to each said sealing part of said sealed chamber, and adapted to partition an inner empty space into a first pressureproof housing area and a second pressureproof housing area;
   an inlet communicating with said first pressureproof housing area partitioned by said filter unit for introducing a substance for treatment by sizing under pressure into said sealed chamber;
   an outlet communicating to said second pressureproof housing area partitioned by said filter unit for discharging the substance after sizing from said sealed chamber; and
   temperature controlling means disposed on an outer surface of said first pressureproof housing for controlling temperature of said substance being introduced for treatment,
   wherein said filter unit comprises:
      a pressureproof supporting means for supporting a supporting plate comprising orifices, said orifices comprising openings with a larger diameter in one surface and openings with a smaller diameter in another surface; and
      a membrane filter disposed on said surface of said supporting plate comprising larger-diameter openings in said first pressureproof housing area.

6. A high-pressure sizing apparatus according to claim 5, wherein said membrane filter comprises micro pores piercing through a thickness of said filter.

7. A high-pressure sizing apparatus according to claim 5, wherein said orifices in said supporting plate are stepped.

8. A high-pressure sizing apparatus according to claim 5, wherein said orifices in said supporting plate have a diameter ratio of larger-diameter openings to smaller-diameter openings in the range of about 1:0.01 to about 1:0.5.

9. A high-pressure sizing apparatus according to claim 5, wherein said membrane filter comprises a film comprising liquid flow paths.

10. A high-pressure sizing apparatus according to claim 9, wherein said membrane filter comprises a thin film comprising minute liquid flow paths arranged in a reticular pattern.

11. A high-pressure sizing apparatus according to claim 5, wherein said orifices of said supporting plate plate have an opening ratio and said one surface provided with orifices opening with a larger diameter comprises a larger diameter opening side of said supporting plate, and the opening ratio on the larger-diameter opening side of said supporting plate is in the range of about 30% to about 90%.

12. A high-pressure sizing apparatus according to claim 5, wherein said one surface comprises a main or major surface of said supporting plate, and said another surface comprises another main or major surface of said supporting plate.

13. A filter unit comprising:
   a supporting plate comprising orifices opening with a larger diameter in one surface and with a smaller diameter in another surface; and
   a membrane filter cassette comprising a membrane filter and a supporting means for supporting said membrane filter, disposed on the surface of said supporting plate comprising openings with a larger diameter.

14. A high-pressure sizing apparatus comprising:
   a sealed chamber comprising a first pressureproof housing comprising a sealing part and a second pressureproof housing comprising a sealing part, each said sealing part comprising an opposed surface in close contact;
   a filter unit set in an area proximate to each said sealing part of said sealed chamber, and adapted to partition an inner empty space into a first pressureproof housing area and a second pressureproof housing area;
   an inlet communicating with said first pressureproof housing area partitioned by said filter unit for introducing a substance for treatment by sizing under pressure into said sealed chamber;

an outlet communicating to said second pressureproof housing area partitioned by said filter unit for discharging the substance after sizing from said sealed chamber; and temperature controlling means disposed on an outer surface of said first pressureproof housing for controlling temperature of said substance being introduced for treatment, wherein said filter unit comprises:

a pressureproof supporting means for supporting a supporting plate comprising orifices, said orifices comprising openings with a larger diameter in one surface and openings with a smaller diameter in another surface; and a membrane filter cassette comprising a membrane filter and a supporting means for supporting said membrane filter, disposed on said surface of said supporting plate comprising larger-diameter openings in said first pressureproof housing area.

* * * * *